United States Patent [19]

Hoffman

[11] Patent Number: 5,035,712
[45] Date of Patent: Jul. 30, 1991

[54] SELF-ADJUSTING PROSTHESIS ATTACHMENT

[75] Inventor: Erik L. Hoffman, Roosendaal, Netherlands

[73] Assignee: Ordev B.V., Netherlands

[21] Appl. No.: 537,922

[22] Filed: Jun. 12, 1990

[30] Foreign Application Priority Data

Jun. 16, 1989 [NL] Netherlands ............... 8901526

[51] Int. Cl.⁵ ................. A61F 2/28; A61F 2/30; A61F 2/36
[52] U.S. Cl. .......................... 623/16; 623/18; 623/23
[58] Field of Search .............. 623/16, 18, 22, 23

[56] References Cited

U.S. PATENT DOCUMENTS

| 4,011,602 | 3/1977 | Rybicki et al. | 623/16 |
|---|---|---|---|
| 4,728,333 | 3/1988 | Masse | 623/23 |
| 4,756,711 | 7/1988 | Mai | 623/23 |
| 4,921,499 | 5/1990 | Hoffman et al. | 623/16 |

FOREIGN PATENT DOCUMENTS

| 0145166 | 6/1985 | European Pat. Off. . | |
|---|---|---|---|
| 0187903 | 7/1986 | European Pat. Off. | 623/23 |
| 0243298A2 | 10/1987 | European Pat. Off. . | |
| 0358399A1 | 3/1990 | European Pat. Off. . | |
| 1548964 | 7/1979 | United Kingdom . | |
| 2055295A | 3/1981 | United Kingdom . | |
| WO86/02260 | 4/1986 | World Int. Prop. O. . | |

Primary Examiner—Ronald Frinks
Attorney, Agent, or Firm—Peter L. Michaelson

[57] ABSTRACT

A tripartite set for securing a prosthesis to a bone, namely,
- a proximal part connected to the prosthesis and adapted to be received in a complementarily processed part of a marrow cavity;
- a distal part or tip to be fixed in said marrow cavity in an advanced position; and
- a tie member connecting said two parts, one end of said tie member extending at said tip and forming a wedge bolt or like member which expands upon the exercise of tensile force therewith, and said tie member being an at least axially resilient element with flat spring characteristics at least in the body temperature range.

13 Claims, 3 Drawing Sheets

SELF-ADJUSTING PROSTHESIS ATTACHMENT

This invention relates to the attachment of a prosthesis in a bone.

It is known to secure a prosthesis, for example, a joint prosthesis, to a long bone by inserting a tapered part of the prosthesis in a portion of the longitudinal cavity in the long bone, which has been given a fitting, complementary shape, and fixing it therein. Various proposals have been made for effecting such fixation. One of these comprises securing the prosthesis by means of a cement, and in another fixation method, use is made of an anchor which is fixed in an advanced position in the marrow cavity and is connected to the tapered part of the prosthesis by a tie member in the form of a metal wire, by means of which the prosthesis is drawn into the complementary tapered portion of the longitudinal cavity, and the prosthesis is stabilized relatively to the bone.

Hitherto known techniques have the disadvantage that, in course of time, play arises between the tapered part of the prosthesis, the prosthesis pin, and the portion of the bone cavity in which the pin is fitted. One cause of this play is so-called micromovements. Causes of such shearing forces occurring in the interface of bone and prosthesis are, on the one hand, the difference in flexibility between bone and prosthesis material, and on the other, the tensile and compressive loads alternately exerted through the prosthesis on the bone during body movements.

According to a prior proposal described in NL-A-8702371 (EP-A-311208), a prosthesis is secured in a bone cavity using a shape memory metal which at a temperature change beyond a given transition point, undergoes a change in shape, i.e., it shrinks or expands, which change in shape is used for correction when the prosthesis has been in use for some time and play has been established, by increasing the active diameter of fastening means of the prosthesis engaging with the inner surface of the bone, so that the prosthesis can be re-fixed by non-surgical means.

One object of the present invention is to provide a prosthesis attachment which avoids the disadvantages of prior techniques, can be optimally adapted to different bone configurations in a simple manner, and takes maximum account of the load on the bone through the prosthesis.

The invention accordingly provides, for placing a prosthesis in a bone, a tripartite set, namely, a proximal part connected to the prosthesis and adapted to be received in a complementarily processed part of a marrow cavity; a distal part or tip to be fixed in said marrow cavity in an advanced position; and a tie member connecting said two parts, one end of said tie member extending at said tip and forming a wedge bolt therewith, or a like element which expands upon the exercise of tensile force, and said tie member being an at least axially resilient element with flat spring characteristics at least in the body temperature range.

In a preferred embodiment of the invention, the tie element is a rod of shape memory metal (NITINOL). Unlike the applicants' above prior proposal, in which the shape memory of the metal is used for heating the rod afterwards beyond a transition temperature, thereby to effect a change in shape, a different property of shape memory metal is used, namely, the presence of so-called superelasticity. By this, the following effect is meant.

A rod stretched at a low temperature, below the transition point of the metal in question, will return to its original length when heated to above the transition point, owing to the shape memory of the material. When this shrinkage is prevented, a shape recovery stress is built up in the metal. The property of shape memory metal, namely, that, throughout a large range of stretch, the stress built up remains constant during the return to the original length is called superelasticity. This effect also occurs by stretching the rod above its deformation temperature, when it changes from fully austenite into the martensitic phase to form stress-induced martensite (SIM), which exhibits the same flat distance/stress curve except that upon return to the austenitic phase the shape recovery stress is at a lower level than when the rod has first been stretched below the transition point.

To secure a prosthesis in a prepared bone, the distal tip with the tie element are introduced into the bone cavity, and the tip is placed in a manner to be described hereinafter; subsequently the proximal part of the attachment assembly is placed in position, connected to the tie member, and a maximum pre-stress within the range of superelasticity is generated in the tie member.

As the tie member is given a pre-stress as the prosthesis is being implanted, which pre-stress remains constant within a large range of stretch, the proximal part will always remain biased in the direction of the distal part with a force which contributes to preventing micromovements.

Preventing micromovements is very important to achieve so-called initial stability, that is to say, that in the first phase after the implantation of the prosthesis, bone tissue is given an opportunity of growing into a porous coating of bio-compatible or bio-active material, such as hydroxy apatite, which is applied to the proximal part of the prosthesis attachment to be inserted into the bone. Micromovements prevent this formation of a natural secure connection between prosthesis and bone.

When use is made of a thin rod of shape memory metal, for example, with a diameter of about 2 mm, and hence having a high flexibility, together with a relatively short proximal part, the following additional advantage is obtained. In a hip joint, the shank inserted into the bone is eccentrically loaded, so that the shank tends to tilt. Hitherto it has been tried to prevent such tilting by using a long shank.

A long shank has a number of disadvantages. One factor which must be taken into account is the so-called "stress-shielding", i.e., that in a bone zone which is loaded below a certain limit, for example, because forces exercised are deflected through a prosthesis member, bone material disappears as a result of resorption.

Unduly loaded bone parts tend to disappear through necrosis. This has been shown in in-vivo experiments with goats. A wedge bolt element with a segmented cylindrical face was placed in a non-round marrow cavity. When the wedge element was expanded, it engaged with circumferentially spaced separate zones of limited dimension, where relatively high pressures were exerted on the bone material. Owing to necrosis, these engagement zones became ever larger, and consequently the specific pressure became lower, until these zones formed a closed cylindrical surface which fittingly enclosed the surface of the wedge element, and whereby, owing to a distribution of the radial forces, a pressure level was reached which could be considered to be optimal, namely, without any further necrosis or resorption, while a perfect press fit is formed by natural means.

In summary, in the case of bone material, both "underload" and "overload" conditions result in material resorption or necrosis by natural means.

With a long prosthesis shank which extends deeply into a bone, there is the danger that the forces introduced are conducted to the distal end, which becomes fixed in the often narrower central part of the bone by means of a press fit forming automatically. As a consequence, the proximal part of the bone would be unloaded, and resorption may occur at that position. The result is play around the proximal part of the prosthesis pin while the distal part becomes fixed. In such a situation movements occur in the proximal part of the bone, which bar the desired initial stabilization.

By using, in accordance with this invention, a short proximal prosthesis part in combination with a flexible rod of shape memory metal, forces introduced are prevented from being displaced to the tip of the prosthesis. They are concentrated in the proximal part of the prosthesis, where they render possible deformation of a press fit by natural means.

As the stress range of superelasticity is far below the threshold stress above which fatigue fracture occurs, the chance thereof is minimal.

In a further elaboration of the invention, the distal tip may be provided with a plurality of circumferentially distributed segments, whose outer surfaces form parts of a cylindrical surface, and whose inner surfaces taper towards one end, one end of the tie member being complementarily wedge-shaped and being disposed between these segments, there being provided means for mechanically fixing said wedge-shaped end in a axial direction relatively to said segments.

For this purpose, use may be made of a sleeve, which may or may not form part of a tensioning device, with an end stop which is slid over said tie member, and through the exercise of force from the proximal end, and through said end stop, forces the segments over the wedged end of said tie member. As a result the segments are moved radially outwards, and the tip becomes fixed within the bone cavity, preferably below or at the level of the narrowest part, the isthmus. This method has the advantage that the sleeve is a protective enclosure of the tie member. A disadvantage could be that the sleeve has an adverse effect on the flexibility of the tie member. This last does not apply, of course, if the sleeve is a part of a tensioning device, as in that case the sleeve is removed after the fixation of the tip.

Another method of fixing the tip is displacing the segments over the wedge end of the tie member by means of a nut which is in engagement with a threaded part of the tie member and can be tightened by means of a torque spanner.

A different preferred embodiment of the tip is a three-membered star (cf the "mercedes star") made of spring steel, with the members having upset ends to form feet, which are roughened to effect a higher shear force. Prior to the introduction into the femur shank, the three members or blades are drawn into a sleeve, so that the members are folded together, and at the desired level of introduction the tip is pushed out of the sleeve, resulting in clamping action owing to the resiliency of the blades. The advantage of this last embodiment is that when the nitinol rod is tensioned no higher stress is exerted on the bone, as this is largely absorbed by the resiliency of the material.

Preferably, the segments of the tip are interconnected and radially movable along guide tracks, if the device is placed at the level of the isthmus. When placed below the isthmus, the tip may be tapered. In the top of the tip, a means is provided for causing the nitinol rod to exit always in the correct axial direction, and thus prevents the rod from being bent or deflected.

When the tip has thus been fixed, the proximal part of the attachment is secured in the fitting cavity in the bone by tensioning the tie member in the range of the superelasticity described. For this purpose use can be made of another property of shape memory metal, namely, a hysteresis in the temperature/stress curve. When, after heating, the metal is cooled, the shape recovery stress remains at the same level through a range of 10°-15° C. It is possible to select a shape memory metal with a higher transition temperature than the body temperature, e.g. 45° C. At this temperature the range of superelasticity extends beyond the body temperature of 37° C., e.g., 7% rather than 6% elongation. After an extension of 7%, the tie member is fixed in the proximal part. Even after the tie member has assumed the body temperature, the shape recovery stress remains in the higher range of superelasticity. During the introduction, a nitinol rod has room temperature of for example 20° C., so that the force with which the rod is stretched is smaller than at the body temperature.

The set of proximal part, tie member and tip according to the invention lends itself excellently to modular construction, so that with a limited stock of parts optimally fitting assemblies can be made.

In an alternative embodiment of the invention the distal end of the tie member is not fixed to a tip but is threaded through a tube arranged in the medial femur-condyl and fixed at the end emerging from the lower end of said tube.

Some embodiments of the self-adjusting prosthesis attachment according to the present invention will now be described, by way of example, with reference to the accompanying drawings, in which FIG. 1 shows diagrammatically a longitudinal part-sectional elevation of a prosthesis secured in a bone;

Figure 1:
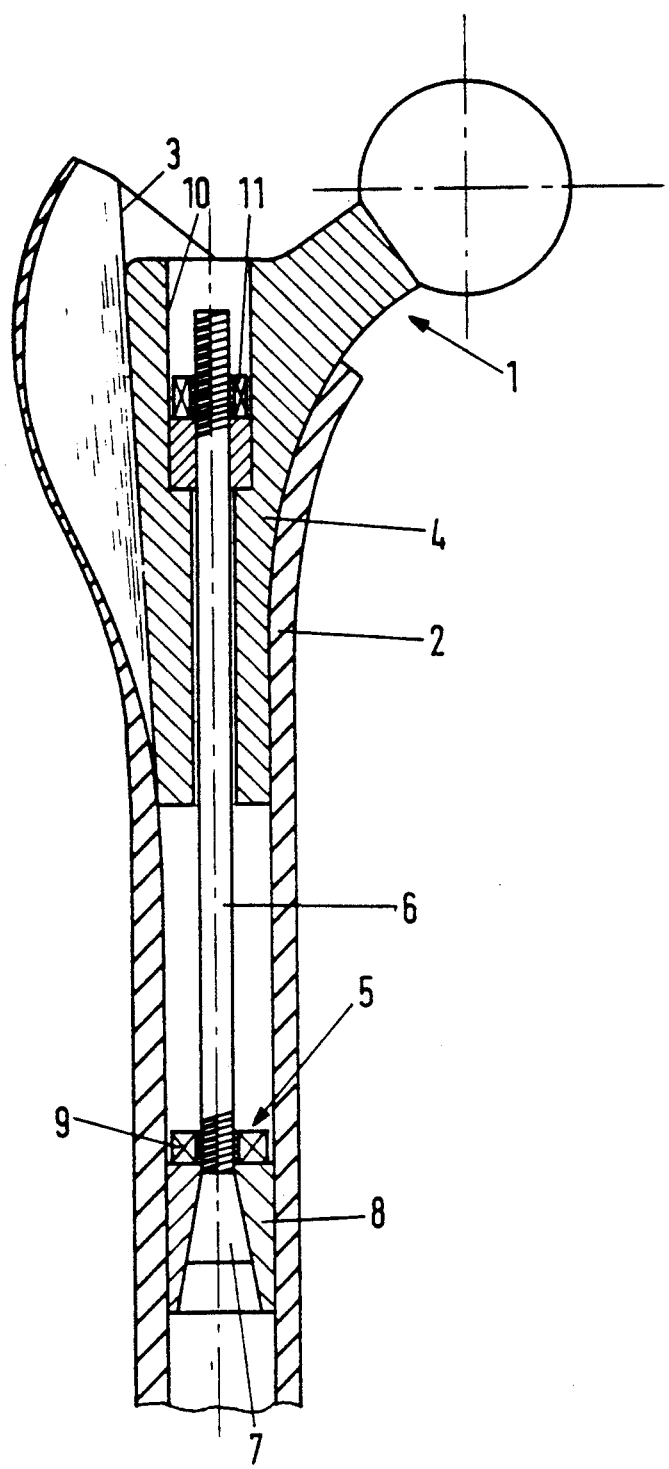

In the embodiment of FIG. 1, a prosthesis 1 forming a part of a hip joint, is secured in a bone 2, the proximal part 3 of which has been prepared to adapt it in shape to the proximal part 4 of an attachment assembly further comprising a tip 5 and a tie member 6. The distal end of tie member 6 includes a wedge-shaped part 7, around which a number of segments 8 are arranged. Segments 8 have an outer wall formed as a part of a cylindrical or conical surface and an inner wall which is at least partly of tapered configuration, complementary to the wedge-shaped end part 7 of tie member 6.

For fixing the tip in the marrow cavity, the segments are pushed over the wedge-shaped end part 7 of the tie member by means of a nut 9 as a result of which the active diameter of the combination of segments is increased, by means of a specially designed tool.

Tensioning the proximal part 4 and thereby putting the tie member 6 under a stress can be effected by means of a nut 11, using the bottom of a recess 10 formed in the proximal part as a counter-bearing, or by means of a specifically designed tool.

The tie member is a rod with a diameter of about 4 mm and made of shape memory metal, in particular NiTi alloys, such as Ni 55 Ti 45, which have the property that they are capable of undergoing a martensitic structural change in the solid state, induced by stress, which is reversible and in the martensitic range has a shape recovery stress of constant value. This effect is called superelasticity.

In this concept, this property is used by stretching the shape memory metal in the austenitic phase, as a result of which it becomes stress-induced martensite, and this in the range with a flat distance/stress curve. When the elongation is consumed, the material automatically returns into the austenitic phase.

When the tip 5 has been fixed in bone 2, tie member 6 is stretched by tightening nut 11 at a temperature higher than the body temperature to within the superelastic or martensitic range associated with the temperature concerned. At a temperature of 45° C., the rod 6 can be stretched by up to 7%. At the body temperature, the maximum elongation is about 6%. So long as the elongation has not been "consumed", the proximal part 4 is pulled in the direction of tip 5 with a constant force. The stress in rod 6 is consumed to prevent play both at the proximal part 4 and at tip 5.

Figure 2:
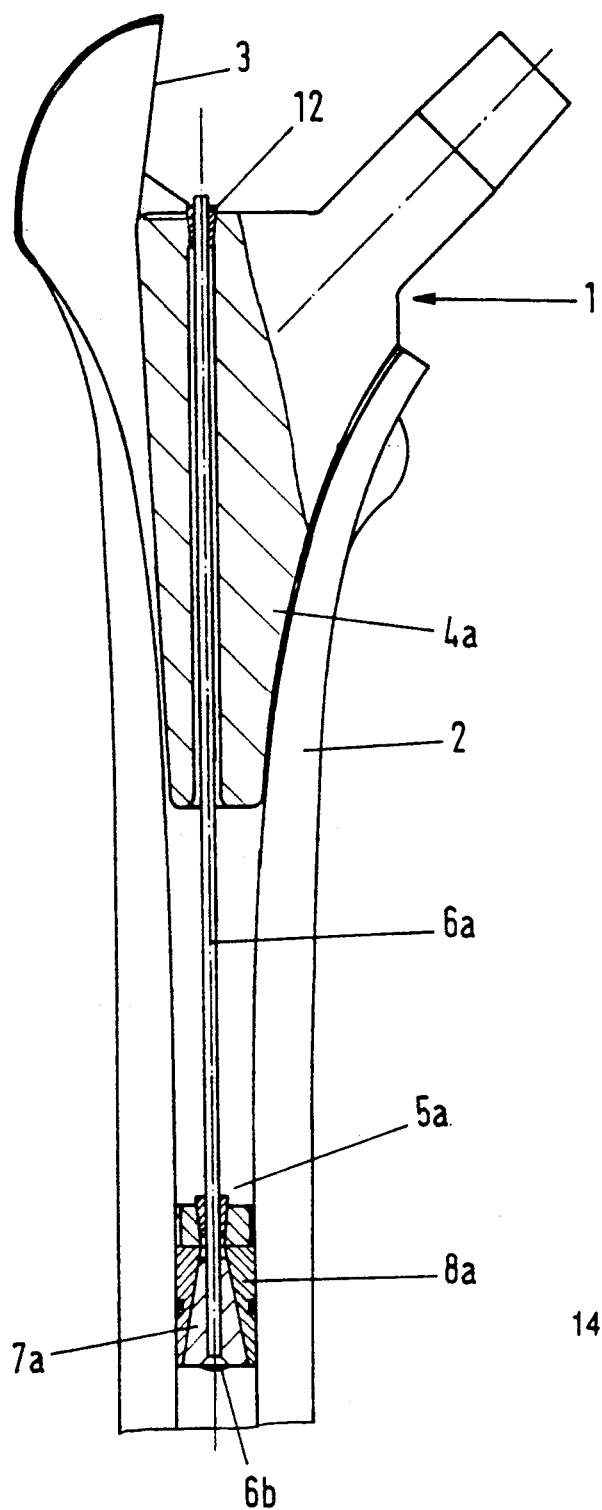
FIG. 2 is a part-sectional elevation similar to FIG. 1, showing a variant embodiment.

In the variant embodiment of FIG. 2, the shape memory spring construction has been simplified, so as to make for a simpler surgical technique.

The shape memory spring is a straight wire 6a with a distal upset flange 6b with which a conical core 7a of a distal tip 5a can be axially displaced in a shell 8a of segments to change the active diameter thereof. For fixing spring 6a relative to the proximal part of prosthesis 4a, use is made of a hollow conical wedge 12.

To secure the prosthesis in a bone, the wedge assembly 7a, 8a of tip 5a is placed at a given depth in the intermedullary canal. The shape memory spring is tensioned whereby the upset flange 6b pulls core 7a into the segmented shell 8a, and thus tip 5a is secured. Subsequently, the shape memory spring, which has a sufficient excess of length, is tensioned and by means of the hollow conical wedge 12 clamped to the proximal part 4a of the prosthesis. The projecting part of spring 6a is cut off.

This procedure is simpler than that which must be followed with the embodiment of FIG. 1. In fact, owing to the absence of threaded zones on the spring, any desired length of spring can be used as a starting product, and hence the tip can be positioned at any desired site. Also, screwing the spring to the proximal prosthesis part, using a torque spanner can be omitted.

As there is no friction between a pre-stress bolt 11 and the proximal part of the prosthesis, the tensioning of the spring is better reproducible. As the spring 6a is more flexible than the thicker spring 6, its flexibility is higher, and locking against loosening from vibration is no longer necessary.

Furthermore, the rod is thinner, simpler and hence less expensive. Other advantages of a smaller diameter and of more flexibility of the rod are that the number of prostheses which must be kept in stock can be reduced, because the flexibility of the spring permits using a symmetrical proximal part. Furthermore, owing to the smaller diameter with equal tensile force, a higher shape recovery stress can be achieved. With an equal hysteresis stress loss between tensioning and relax phase of the shape memory spring, the femur needs to be overloaded to a lesser extent during tensioning.

Figure 3:
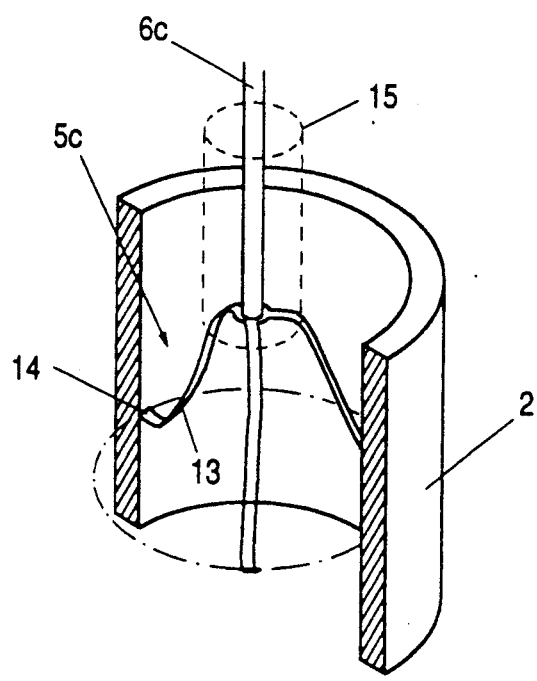
FIG. 3 is a diagrammatic illustration of a different embodiment of tip.

FIG. 3 diagrammatically shows a variant embodiment of the tip with a shape memory spring 6c of nitinol or other spring material, for instance maragin steel. Attached to the lower end of spring 6c are three downwardly diverging members or blades 13 of spring steel with hooks 14. To introduce tip 5c, use is made of a sleeve 15, which keeps blades 13 in folded-together condition. When tip 5c has been placed in position, sleeve 15 is pulled up. Blades 13 then spring outwards and the hooks become fixed in bone 2 during the contraction of spring 6c.

Figure 4:
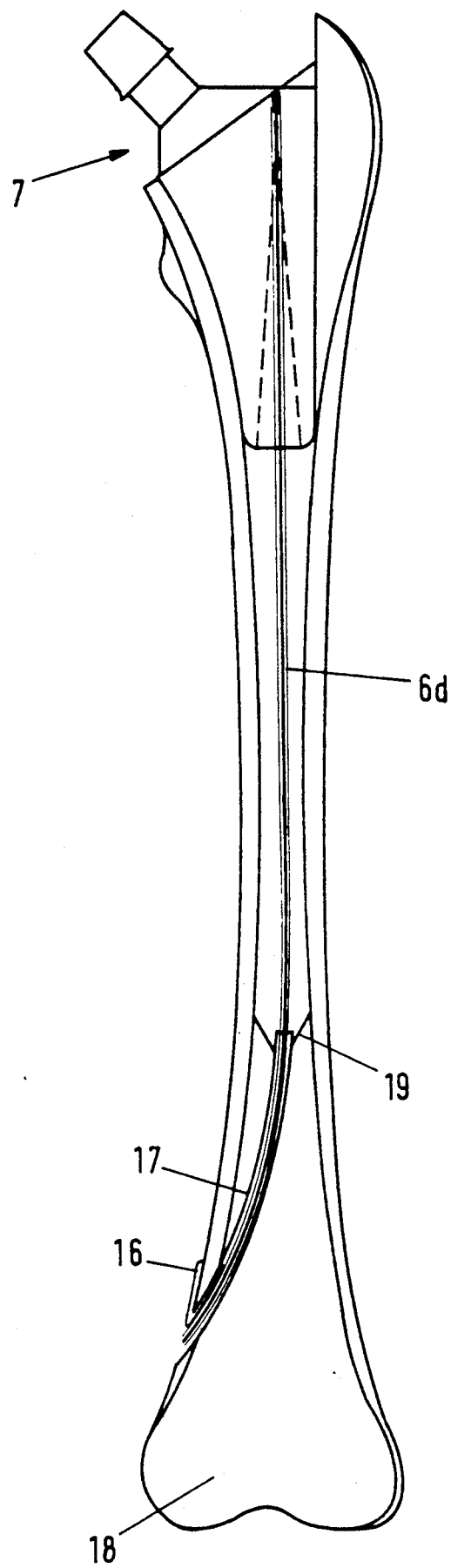
FIG. 4 shows an alternative embodiment of the prosthesis.

In the alternative embodiment of FIG. 4 the memory spring 6d is threaded through a tube 17 arranged in the medial femurcondyl 18. After tensioning either distally or proximally, the distal end of spring 6d is fixed to a plate 16 at the outside of 18. The proximal end of tube 17 is positioned by a centralizer 19.

I claim:

1. A tripartite set for securing a prosthesis (1) to a bone (2), namely,
    a proximal part (4) connected to the prosthesis and adapted to be received in a complementarily processed part (3) of a marrow cavity;
    a distal part or tip (5) to be fixed in said marrow cavity in an advanced position; and
    a tie member (6) connecting said two parts, one end of said tie member extending at said tip and forming a wedge bolt or like member which expands upon the exercise of tensile force therewith, and said tie member being an at least axially resilient element with flat spring characteristics at least in the body temperature range.

2. A prosthesis attachment as claimed in claim 1, wherein the tie element is a rod (6) of shape memory metal.

3. A prosthesis attachment as claimed in claim 2, wherein the rod of shape memory metal (6) has a diameter of about 2 mm and hence a high flexibility.

4. A prosthesis attachment as claimed in claim 1, characterized in that the distal tip (5) is provided with a plurality of circumferentially distributed segments (8), whose outer surfaces form parts of a cylindrical surface or conical surface, and whose inner surfaces taper towards one end, one end (7) of the tie member being substantially complementarily wedge-shaped and being disposed between the segments (8), there being provided means (9) for mechanically fixing said wedge-end (7) in axial direction relatively to said wedge segments (8) and the tie member.

5. A prosthesis attachment as claimed in claim 4, characterized by a sleeve which may or may not form part of a tensioning tool with an end stop which is slid over said tie member and through the exercise of force from the proximal end, and through said end stop, forces the segments over the wedged end of said tie member, and fixes it to the tie member.

6. A prosthesis attachment as claimed in claim 4, characterized by a nut (9) in operative association with a threaded portion of said tie member, said nut being arranged to be tightened with a spanner from the proximal end to fix said tip (5).

7. A prosthesis attachment as claimed in claim 1, characterized by a modular construction of the constituent parts.

8. A prosthesis attachment as claimed in claims 2, wherein the shape memory metal of the tie member is an NiTi alloy.

9. A prosthesis attachment as claimed in claim 2, wherein the rod of shape memory metal (6a) has a diameter of about 1.5 mm.

10. A prosthesis attachment as claimed in claim 9, wherein the distal tip (5a) is provided with a plurality of circumferentially distributed segments (8a), whose outer surfaces form parts of a cylindrical surface, and whose inner surfaces taper towards one end, here being further provided a core (7a) of substantially complementary wedge shape, said core being disposed between said segments (8a) and said memory metal (6a) has an upset flange (6b) engaging with said core (7a).

11. A prosthesis attachment as claimed in claim 10, characterized by a hollow conical wedge (12) for the exercise of power on, and the fixation of, said memory metal (6a) on the proximal part (4a) of the prosthesis (1).

12. A prosthesis attachment as claimed in claim 1, wherein the distal tip is provided with three circumferentially distributed blades made of spring steel and diverting downwardly and outwardly from the end of said tie member with hooks extending outwardly and upwardly at the free lower ends of said blades.

13. A tripartite set for securing a prosthesis (1) to a bone (2), namely,
- a proximal part (4) connected to the prosthesis and adapted to be received in a complementarily processed part (3) of a marrow cavity;
- a distal part in the form of a plate member (16) to be fixed in an advanced position such as adjacent the medial femurcondyl; and
- a tie member (6) connecting said two parts, one end of said tie member extending through a distally arranged threading tube adapted to be inserted in said medial femurcondyl and fixed at the outer face thereof, said tie member being an at least axially resilient element with flat spring characteristics at least in the body temperature range.

* * * * *